United States Patent [19]

Ellenberg, III

[11] Patent Number: 5,474,094
[45] Date of Patent: Dec. 12, 1995

[54] CUT RIB PROTECTOR

[76] Inventor: William B. Ellenberg, III, P.O. Box 605, Bogart, Ga. 30622

[21] Appl. No.: 286,002

[22] Filed: Aug. 4, 1994

[51] Int. Cl.[6] ................................................. A61F 13/00
[52] U.S. Cl. ................................................. 128/888; 606/69
[58] Field of Search ................................. 128/845, 846, 128/888; 606/69, 70, 71, 215, 216; 411/466, 467, 468, 461; 52/690, 712

[56] References Cited

U.S. PATENT DOCUMENTS

| | | | |
|---|---|---|---|
| 4,000,737 | 1/1977 | Horn | 128/888 |
| 4,134,399 | 1/1979 | Halderson | 128/888 |
| 4,201,215 | 5/1980 | Crossett | 606/216 |
| 4,327,715 | 5/1982 | Corvisier | 606/71 |
| 4,583,541 | 4/1986 | Barry | 606/69 |
| 5,094,233 | 3/1992 | Brennan | 602/17 |
| 5,133,718 | 7/1992 | Mao | 606/69 |
| 5,139,498 | 8/1992 | Astudillo | 606/69 |

*Primary Examiner*—Michael A. Brown
*Attorney, Agent, or Firm*—James B. Middleton

[57] ABSTRACT

A rib protector slips over the cut ends of ribs to protect a person working in the thoracic cavity. In an autopsy or the like wherein the front of the rib cage has been cut away to provide access to the thoracic cavity, the cut ends of the ribs are rough and splintery. The rib protector is tough and thick enough that splinters will not pass through the protector. The protector encases the ends of all the cut ribs, one protector being on each side of the rib cage. Adhesive, natural clamping of the protector, or the like can hold the protector in place. The protector may be made in any size, and will be easily cut for final adjustment of the size.

14 Claims, 1 Drawing Sheet

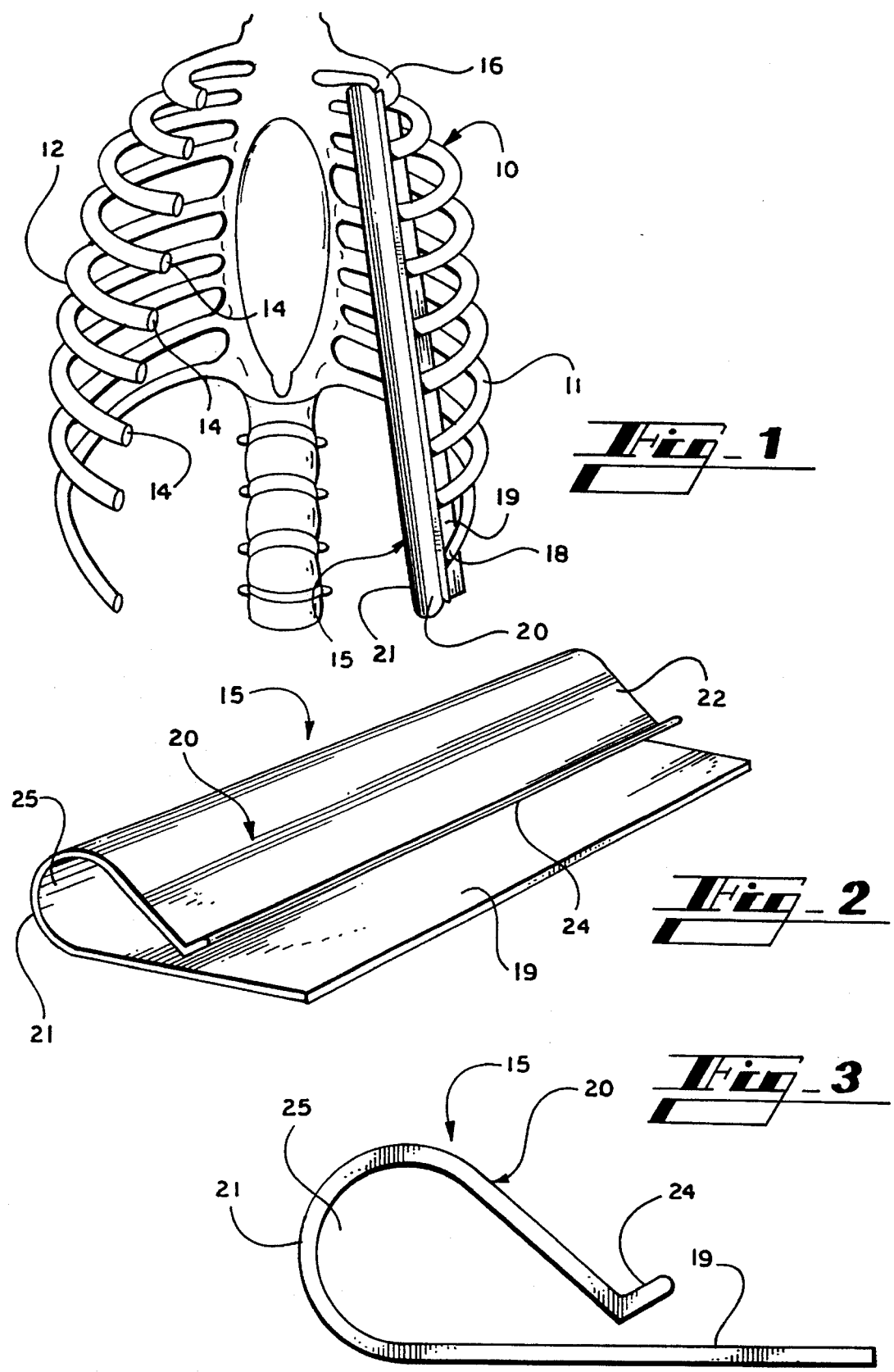

CUT RIB PROTECTOR

BACKGROUND OF THE INVENTION

1. Field of the Invention

This invention relates generally to protective coverings, and is more particularly concerned with a protective covering for the cut ends of ribs during an autopsy or the like.

2. Discussion of the Prior Art

When an autopsy is performed on a body, it is standard practice to cut away a portion of the rib cage to provide access to the thoracic cavity of the body. The rib cage is cut on each side of the sternum, from the top to the bottom ribs, so the entire front of the rib cage is removed to provide the desired access. The problem with this procedure is that the cut ends of the ribs are generally quite rough, frequently being somewhat splintered. Thus, while the pathologist has a large opening for access to the thoracic cavity of the body, the rough rib ends present a constant hazard that can pierce or tear a glove, and of course pierce or tear the pathologist's skin as well.

A torn glove is always some threat to medical personnel, and if the flesh is also damaged there is a great risk of infection. The past diseases such as hepatitis are bad; but, today the threat is frequently AIDS, which is considerably worse since there is still no known cure.

In the past, some pathologists simply made an effort to be careful and not engage the rough end of a cut rib. It will be understood that this is quite difficult if one is to examine all the tissue in the body. Alternatively, people have attempted to cover the rib ends with a towel, or a surgical drape or the like. Something bulky, like a towel, is difficult to keep in place, and may interfere with the pathologist's work. Lighter weight materials such as a surgical drape may not be thick enough to guard against all the splinters and such, and is still difficult to keep in place over the cut ends of the ribs without encroaching on the work site.

There is a further problem with the cut ribs in that, after the autopsy has been completed, the body will be transferred to a mortician to be prepared for burial or other disposal. Typically, the pathologist places the visceral organs into a plastic bag, and the bag is left within the body cavity. Thus, the mortician must remove the viscera bag to begin preparation of the body. The rough rib ends sometimes snag the viscera bag, causing a large mess to be cleaned up. Further, when the mortician is working on the body, the mortician must work in the thoracic cavity, and is likely to damage the gloves and flesh as discussed above.

Thus, the prior art has not provided a solution to the hazardous situation of the rough rib ends, though the hazard has existed for many years.

SUMMARY OF THE INVENTION

The present invention provides a cut rib protector in the form of a guard that is received over the cut ends of a plurality of ribs. The protector, or guard, is formed of a tough and durable material that will not severely degrade during the procedure being performed; and, means are provided for holding the protector in place over the cut ends so the protector will not be inadvertently displaced.

The preferred embodiment of the invention comprises a strip long enough to extend from the top-most to the bottom-most cut ribs. Thus, two protectors will be used on one body: one to cover the left side of the ribs, and one to cover the right side of the ribs. The protectors are thick enough, and tough enough, that even the worst of splinters cannot pierce the protectors, and the person working in the body cavity cannot be injured by the cut rib ends.

BRIEF DESCRIPTION OF THE DRAWINGS

These and other features and advantages of the present invention will become apparent from consideration of the following specification when taken in conjunction with the accompanying drawings in which:

FIG. 1 is a perspective view showing a rib cage with the front of the rib cage cut away, and showing one rib protector made in accordance with the present invention in place on the left side of the rib cage;

FIG. 2 is an enlarged perspective view of the rib protector shown in FIG. 1; and, FIG. 3 is an end elevational view of the device shown in FIG. 2.

DETAILED DESCRIPTION OF THE EMBODIMENT

Referring now more particularly to the drawings, and to that embodiment of the invention here shown by way of illustration, FIG. 1 shows a rib cage generally designated at 10, having a left side 11 and a right side 12. The front portion of the rib cage 10 has been cut away as is conventional for performing an autopsy.

As illustrated in FIG. 1, the cut rib ends 14 on the right side of the rib cage are not covered. It will therefore be readily seen that the rough ends 14 are so disposed as to be difficult to avoid when working inside the thoracic cavity.

The protector of the present invention is shown covering the rib ends on the left side of the rib cage. The protector is generally indicated at 15, and is shown extending from the top cut rib 16 to the bottom cut rib 18. As will be discussed in detail below, the protector 15 includes a bottom plate 19 and a top plate 20 joined by a bight portion 21. The protector can be slipped into place over the cut ends of the ribs and held in place as needed.

Attention is directed to FIGS. 2 and 3 of the drawings for a more detailed description of the particular embodiment of the invention here presented. It will be seen that the protector 15 is formed integrally, the bottom plate 19 being generally flat. The material then curves through the bight portion 21 and continues to form the top plate 20.

As shown in FIGS. 2 and 3, the top plate 20 is angled towards the base plate 19 as at 22, and terminates in an upwardly turned edge, or divergent edge 24. The bight portion 21 is rather large for defining a wide throat area 25, and the top plate 20 converges with the bottom plate 19 to restrict this throat. The result is a clamping arrangement which will assist in holding the protector 15 in place.

It will therefore be understood that the protector 15 will be made of a somewhat elastic material, and the divergent edge 24 can be urged away from the bottom plate 19. One can therefore simply place the bottom plate 19 within the rib cage with the cut ends of the ribs bearing against the edge 24, and a small amount of pressure will cause the top plate to move away from the bottom plate 19 to allow the ribs to enter the throat 25. The spring action of the top plate 20 will assist in retaining the device in place, though adhesives or the like may be included if desired.

It is contemplated that the protector of the present invention will be made in any desired length, and that the protector will be easy to cut to the length needed. Many different materials can be used for the protector and provide the qualities needed. Many polymeric materials, such as polyolefins, polystyrene, polyurethanes, polytetraflouroethylene, nylon, polysiloxane, polyester and the like can be used. Any polymeric material that has enough toughness to prevent piercing by bone splinters can be used, and this includes most of the polymeric materials currently in use. Further, the device may be made of metals, including aluminum, copper, brass etc., or rubber, including both natural and synthetic rubbers. When using a metal, of course, the material could be quite thin, and may still be easily cut with scissors. The protector device may even be made of wood or paper if desired. One may use a molded paper or other fibrous material, or a formed cardboard or the like may be used.

The dimensions of the protector are quite variable as desired. For example, the width of the top and bottom plates may be as narrow as around 0.25" or 0.6 cm., and may be as wide as about 5" or 12 cm. The length of the protector may be around 14" or 35 cm. Obviously, if the protector is being made for a particular type of person, the dimensions can be confined to a narrow range; but, if the protector is being made for the average person, some mid-range compromise may be used. It should also be kept in mind that the protectors can always be easily cut when there are minor problems with the fit.

It will also be understood by those skilled in the art that the top plate 20 does not necessarily form a clamping member, but may extend generally parallel to the bottom plate 19. In this event, the protector will be held in place by other means, such as an adhesive. The adhesive may be applied just before the protector is installed, or the protector may be provided with adhesive at the time of manufacture. Various adhesives can be used, including acrylic, urethanes, polysiloxanes and the like, or gum based adhesives and other well known adhesives.

In using the device of the present invention, the rib cage would be cut as shown in FIG. 1, though fewer ribs may be cut if desired. A protector 15 will then be provided, and cut to length if necessary. The protector 15 should extend to cover the cut ends of all cut ribs. As soon as a protector is in place on one side of the rib cage, the same procedure will be followed to cover the cut ribs on the opposite side of the rib cage. As is mentioned above, one may rely on the clamping action of the top plate 20 with respect to the bottom plate 19, or one may utilize an adhesive, staple or other holding means to secure the protectors 15 in place.

If the ribs are cut during an autopsy, the pathologist may simply leave the protectors 15 in place, and lay the front of the rib cage in place for the body to be transferred to a mortician. The protectors 15 would therefore be already in place for the mortician's protection. The mortician can also leave the protectors in place, and the body can be closed for disposition.

It will therefore be seen that the present invention provides a very simple rib cover for the protection of a person working around the cut ribs. The device is inexpensive, yet effective, and can take many different forms as desired.

It will therefore be understood by those skilled in the art that the particular embodiment of the invention here presented is by way of illustration only, and is meant to be in no way restrictive; therefore, numerous changes and modifications may be made, and the full use of equivalents resorted to, without departing from the spirit or scope of the invention as outlined in the appended claims.

I claim:

1. A cut rib protector for covering the ends of ribs after a portion of a rib cage has been cut away to provide access to the thoracic cavity, said rib protector comprising a bottom plate disposed within the rib cage and extending from the top-most cut rib to the bottom-most cut rib adjacent to the cut end of the cut ribs, a top plate disposed outside the rib cage and extending from the top-most cut rib to the bottom-most cut rib adjacent to the cut end of the cut ribs, and a bight portion connecting said bottom plate and said top plate, said bight portion covering the cut ends of the cut ribs, and means for retaining said protector in place.

2. A cut rib protector as claimed in claim 1, wherein said bottom plate and said top plate are fixed to said bight portion, and converge in the direction away from said bight portion.

3. A cut rib protector as claimed in claim 2, wherein said protector is formed of a resilient material so that said top plate and said bottom plate are resiliently urged towards each other, and wherein such resilient urging constitutes said means for retaining said protector in place.

4. A cut rib protector as claimed in claim 3, and further including a divergent edge carried by said top plate and diverging from said bottom plate in the direction away from said bight portion 5. A cut rib protector as claimed in claim 4, and further including an adhesive for adhering said protector to the ribs.

6. A cut rib protector as claimed in claim 1, wherein said protector is integrally formed, and said means for retaining said protector in place comprises a quantity of adhesive between said top plate and said bottom plate.

7. A cut rib protector as claimed in claim 1, wherein said top plate has a width from 0.6 cm. to 12 cm.

8. A cut rib protector as claimed in claim 7, wherein said top plate has a length around 35 cm.

9. A cut rib protector as claimed in claim 1, wherein said protector is formed of a material selected from the group consisting of polymeric materials, metals, rubbers and fibrous materials.

10. A cut rib protector as claimed in claim 1, wherein said protector is formed of a material selected from the group consisting of polyolefins, polystyrene, polyurethanes, polytetraflouroethylene, nylon, polysiloxane, polyester, aluminum, copper, brass, natural rubber, synthetic rubber, wood and paper.

11. In a body having a rib cage comprising a plurality of ribs and a sternum centrally of the front of said rib cage, at east some of said plurality of ribs being cut on both sides of the sternum to remove a front portion of said ribs yielding cut rib ends in said rib cage, the combination therewith of a cut rib protector, said rib protector comprising a bottom plate disposed within said rib cage and having sufficient length to be adjacent to said cut rib ends, a top plate disposed outside said rib cage and having a length substantially equal to the length of said bottom plate, and a bight portion connecting said bottom plate and said top plate, said bight portion covering said cut rib ends, and means for retaining said rib protector in place.

12. The combination as claimed in claim 11, wherein said rib protector is formed of a resilient material so that said top plate and said bottom plate are resiliently urged towards each other, and wherein such resilient urging constitutes said means for retaining said rib protector in place.

13. The combination as claimed in claim 11, and further including an adhesive for adhering said rib protector to said ribs, said adhesive constituting said means for retaining said rib protector in place.

14. The combination as claimed in claim 11, wherein said rib protector further includes a divergent edge carried by said top plate and diverging away from said bottom plate in the direction away from said bight portion.

* * * * *